(12) United States Patent
Seykora et al.

(10) Patent No.: US 9,237,910 B2
(45) Date of Patent: Jan. 19, 2016

(54) CLIP FOR RIB STABILIZATION

(71) Applicant: Acute Innovations LLC, Hillsboro, OR (US)

(72) Inventors: Andrew W. Seykora, Portland, OH (US); Oren S. Bernstein, Portland, OR (US); Eric Thorsell, Portland, OR (US); Joel Gillard, Portland, OR (US); Kyle A. Loucks, Ridgefield, WA (US)

(73) Assignee: Acute Innovations LLC, Hillsboro, OR (US)

( * ) Notice: Subject to any disclaimer, the term of this patent is extended or adjusted under 35 U.S.C. 154(b) by 164 days.

(21) Appl. No.: 13/752,188

(22) Filed: Jan. 28, 2013

(65) Prior Publication Data

US 2013/0197521 A1    Aug. 1, 2013

Related U.S. Application Data

(60) Provisional application No. 61/590,955, filed on Jan. 26, 2012.

(51) Int. Cl.
| | | |
|---|---|---|
| *A61B 17/56* | (2006.01) | |
| *A61B 17/58* | (2006.01) | |
| *A61B 17/064* | (2006.01) | |
| *A61B 17/84* | (2006.01) | |
| *A61F 2/30* | (2006.01) | |
| *A61B 17/80* | (2006.01) | |

(52) U.S. Cl.
CPC ................................. *A61B 17/8076* (2013.01)

(58) Field of Classification Search
CPC .... A61B 17/8076; A61B 17/82; A61B 17/80; A61B 17/8085

USPC ............ 606/74, 75, 324, 228, 233, 280–299, 606/70, 71, 905
See application file for complete search history.

(56) References Cited

U.S. PATENT DOCUMENTS

| | | |
|---|---|---|
| 20,503 A | 6/1858 | Morse |
| 820,503 A | 5/1906 | Krengel et al. |
| 869,697 A | 10/1907 | Eilhauer et al. |
| 1,105,105 A | 7/1914 | Sherman |

(Continued)

FOREIGN PATENT DOCUMENTS

| | | |
|---|---|---|
| AU | 8975091 A | 2/1992 |
| CA | 2452127 A1 | 12/1993 |

(Continued)

OTHER PUBLICATIONS

Depuy, Inc., McBride S.M.O. Stainless Steel Bone Plates brochure, 1943.

(Continued)

*Primary Examiner* — Kevin T Truong
*Assistant Examiner* — Si Ming Ku
(74) *Attorney, Agent, or Firm* — Kolisch Hartwell, P.C.

(57) ABSTRACT

System, including methods, apparatus, and kits, for rib stabilization. The system may comprise a clip member having a bridge region and a pair of leaf portions connected to each other by the bridge region. The clip member may be configured to be placed on a rib bone with the leaf portions disposed on opposite sides of the rib bone. The system also may comprise a securing member, such as a suture, to attach the clip member to the rib bone, with the securing member extending at least twice between the leaf portions.

21 Claims, 5 Drawing Sheets

(56) References Cited

U.S. PATENT DOCUMENTS

| | | |
|---|---|---|
| 1,156,440 A | 10/1915 | Smith |
| 1,345,425 A | 7/1920 | Wells |
| 1,789,060 A | 1/1931 | Weisenbach |
| 1,889,239 A | 11/1932 | Crowley |
| 1,950,799 A | 3/1934 | Jones |
| 2,406,832 A | 9/1946 | Hardinge |
| 2,443,363 A | 6/1948 | Toensend et al. |
| 2,489,870 A | 11/1949 | Dzus |
| 2,494,229 A | 1/1950 | Collison |
| 2,496,126 A | 1/1950 | Haboush |
| 2,500,370 A | 3/1950 | McKibbin |
| 2,500,993 A | 3/1950 | Mason |
| 2,526,959 A | 10/1950 | Lorenzo |
| 2,579,968 A | 12/1951 | Rush |
| 2,580,821 A | 1/1952 | Nicola |
| 2,583,896 A | 1/1952 | Siebrandt |
| 2,737,835 A | 3/1956 | Herz |
| 3,025,853 A | 3/1962 | Mason |
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,357,432 A | 12/1967 | Sparks |
| 3,386,437 A | 6/1968 | Treace |
| 3,477,429 A | 11/1969 | Sampson |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,716,050 A | 2/1973 | Johnston |
| 3,726,279 A | 4/1973 | Barefoot et al. |
| 3,741,205 A | 6/1973 | Markolf et al. |
| 3,759,257 A | 9/1973 | Fischer et al. |
| 3,774,244 A | 11/1973 | Walker |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,000,525 A | 1/1977 | Klawitter et al. |
| 4,011,863 A | 3/1977 | Zickel |
| 4,055,172 A | 10/1977 | Ender et al. |
| 4,091,806 A | 5/1978 | Aginsky |
| 4,119,092 A | 10/1978 | Gil |
| 4,135,507 A | 1/1979 | Harris |
| 4,169,470 A | 10/1979 | Ender et al. |
| 4,187,840 A | 2/1980 | Watanabe |
| 4,187,841 A | 2/1980 | Knutson |
| 4,201,215 A | 5/1980 | Crossett et al. |
| 4,263,904 A | 4/1981 | Judet |
| 4,327,715 A | 5/1982 | Corvisier |
| 4,364,382 A | 12/1982 | Mennen |
| 4,378,607 A | 4/1983 | Wadsworth |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,473,069 A | 9/1984 | Kolmert |
| 4,483,335 A | 11/1984 | Tornier |
| 4,484,570 A | 11/1984 | Sutter et al. |
| 4,493,317 A | 1/1985 | Klaue |
| 4,503,847 A | 3/1985 | Mouradian |
| 4,506,662 A | 3/1985 | Anapliotis |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,630,601 A | 12/1986 | Harder et al. |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,733,654 A | 3/1988 | Marino |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,828,492 A | 5/1989 | Agnone |
| 4,867,144 A | 9/1989 | Karas et al. |
| 4,892,093 A | 1/1990 | Zamowski et al. |
| 4,893,619 A | 1/1990 | Dale et al. |
| 4,896,661 A | 1/1990 | Bogert et al. |
| 4,903,691 A | 2/1990 | Heinl |
| 4,905,679 A | 3/1990 | Morgan |
| 4,915,092 A | 4/1990 | Firica et al. |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,013,314 A | 5/1991 | Firica et al. |
| 5,013,315 A | 5/1991 | Barrows |
| 5,015,248 A | 5/1991 | Burstein et al. |
| 5,021,056 A | 6/1991 | Hofmann et al. |
| 5,035,697 A | 7/1991 | Frigg |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,116,335 A | 5/1992 | Hannon et al. |
| 5,129,899 A | 7/1992 | Small et al. |
| 5,133,718 A | 7/1992 | Mao |
| 5,135,527 A | 8/1992 | Ender |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,736 A | 4/1993 | Strauss |
| 5,201,737 A | 4/1993 | Leibinger et al. |
| 5,234,431 A | 8/1993 | Keller |
| 5,254,119 A | 10/1993 | Schreiber |
| 5,261,908 A | 11/1993 | Campbell, Jr. |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,356,410 A | 10/1994 | Pennig |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Tom Du Toit |
| 5,423,826 A | 6/1995 | Coates et al. |
| 5,443,483 A | 8/1995 | Kirsch |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Procter et al. |
| 5,531,745 A | 7/1996 | Ray |

(56) References Cited

U.S. PATENT DOCUMENTS

| | | |
|---|---|---|
| 5,534,027 A | 7/1996 | Hodorek |
| 5,545,228 A | 8/1996 | Kambin |
| 5,564,302 A | 10/1996 | Watrous |
| 5,571,103 A | 11/1996 | Bailey |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,603,715 A | 2/1997 | Kessler |
| 5,607,426 A | 3/1997 | Ralph et al. |
| 5,643,261 A | 7/1997 | Schafer et al. |
| 5,643,265 A | 7/1997 | Errico et al. |
| 5,645,599 A | 7/1997 | Samani |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,665 A | 10/1997 | Bryan |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,814,047 A | 9/1998 | Emilio et al. |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo et al. |
| 5,968,046 A | 10/1999 | Castleman |
| 5,968,047 A | 10/1999 | Reed |
| 5,973,223 A | 10/1999 | Tellman et al. |
| 6,001,099 A | 12/1999 | Huebner |
| 6,004,323 A | 12/1999 | Park et al. |
| 6,004,353 A | 12/1999 | Masini |
| 6,007,535 A | 12/1999 | Rayhack et al. |
| 6,007,538 A | 12/1999 | Levin |
| 6,022,350 A | 2/2000 | Ganem |
| 6,027,504 A | 2/2000 | McGuire |
| 6,053,915 A | 4/2000 | Bruchmann |
| 6,077,266 A | 6/2000 | Medoff |
| 6,077,271 A | 6/2000 | Huebner et al. |
| 6,093,188 A | 7/2000 | Murray |
| 6,096,040 A | 8/2000 | Esser |
| 6,113,603 A | 9/2000 | Medoff |
| 6,117,139 A | 9/2000 | Shino |
| 6,117,160 A | 9/2000 | Bonutti |
| 6,123,709 A | 9/2000 | Jones |
| 6,129,728 A | 10/2000 | Schumacher et al. |
| 6,129,730 A | 10/2000 | Bono et al. |
| 6,139,548 A | 10/2000 | Errico |
| 6,152,927 A | 11/2000 | Farris et al. |
| 6,159,213 A | 12/2000 | Rogozinski |
| 6,179,839 B1 | 1/2001 | Weiss et al. |
| 6,183,475 B1 | 2/2001 | Lester et al. |
| 6,193,721 B1 | 2/2001 | Michelson |
| 6,197,028 B1 | 3/2001 | Ray et al. |
| 6,197,037 B1 | 3/2001 | Hair |
| 6,221,073 B1 | 4/2001 | Weiss et al. |
| 6,224,602 B1 | 5/2001 | Hayes |
| 6,228,087 B1 | 5/2001 | Fenaroli et al. |
| 6,235,033 B1 | 5/2001 | Brace et al. |
| 6,235,034 B1 | 5/2001 | Bray |
| 6,238,396 B1 | 5/2001 | Lombardo |
| 6,258,092 B1 | 7/2001 | Dall |
| 6,261,291 B1 | 7/2001 | Talaber et al. |
| 6,273,889 B1 | 8/2001 | Richelsoph |
| 6,280,446 B1 | 8/2001 | Blackmore |
| 6,283,969 B1 | 9/2001 | Grusin et al. |
| 6,290,703 B1 | 9/2001 | Ganem |
| 6,302,883 B1 | 10/2001 | Bono |
| 6,302,884 B1 | 10/2001 | Wellisz et al. |
| 6,302,887 B1 | 10/2001 | Spranza et al. |
| 6,306,136 B1 | 10/2001 | Baccelli |
| 6,312,431 B1 | 11/2001 | Asfora |
| 6,315,779 B1 | 11/2001 | Morrison et al. |
| 6,322,562 B1 | 11/2001 | Wolter |
| 6,325,803 B1 | 12/2001 | Schumacher et al. |
| 6,331,179 B1 | 12/2001 | Freid et al. |
| 6,336,927 B2 | 1/2002 | Rogozinski |
| 6,338,734 B1 | 1/2002 | Burke et al. |
| 6,342,055 B1 | 1/2002 | Eisermann et al. |
| 6,342,075 B1 | 1/2002 | MacArthur |
| 6,355,036 B1 | 3/2002 | Nakajima |
| 6,355,041 B1 | 3/2002 | Martin |
| 6,355,042 B2 | 3/2002 | Winquist et al. |
| 6,358,250 B1 | 3/2002 | Orbay |
| 6,364,881 B1 | 4/2002 | Apgar et al. |
| 6,364,882 B1 | 4/2002 | Orbay |
| 6,364,883 B1 | 4/2002 | Santilli |
| 6,379,354 B1 | 4/2002 | Rogozinski |
| 6,379,359 B1 | 4/2002 | Dahners |
| 6,379,364 B1 | 4/2002 | Brace et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,436,103 B1 | 8/2002 | Suddaby |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,503,250 B2 | 1/2003 | Paul |
| 6,508,819 B1 | 1/2003 | Orbay |
| 6,514,274 B1 | 2/2003 | Boucher et al. |
| 6,520,965 B2 | 2/2003 | Chervitz et al. |
| 6,527,775 B1 | 3/2003 | Warburton |
| 6,533,789 B1 | 3/2003 | Hall, IV et al. |
| 6,547,790 B2 | 4/2003 | Harkey, III et al. |
| 6,565,570 B2 | 5/2003 | Sterett et al. |
| 6,572,620 B1 | 6/2003 | Schon et al. |
| 6,592,578 B2 | 7/2003 | Henniges et al. |
| 6,595,993 B2 | 7/2003 | Donno et al. |
| 6,602,255 B1 | 8/2003 | Campbell et al. |
| 6,623,486 B1 | 9/2003 | Weaver et al. |
| 6,623,487 B1 | 9/2003 | Goshert |
| 6,682,531 B2 | 1/2004 | Winquist et al. |
| 6,682,533 B1 | 1/2004 | Dinsdale et al. |
| 6,689,139 B2 | 2/2004 | Horn |
| 6,695,846 B2 | 2/2004 | Richelsoph et al. |
| 6,706,046 B2 | 3/2004 | Orbay et al. |
| 6,712,820 B2 | 3/2004 | Orbay |
| 6,719,759 B2 | 4/2004 | Wagner et al. |

(56) References Cited

U.S. PATENT DOCUMENTS

| | | |
|---|---|---|
| 6,730,090 B2 | 5/2004 | Orbay et al. |
| 6,730,091 B1 | 5/2004 | Pfefferle et al. |
| 6,736,819 B2 | 5/2004 | Tipirneni |
| 6,767,351 B2 | 7/2004 | Orbay et al. |
| 6,793,658 B2 | 9/2004 | LeHuec et al. |
| 6,821,278 B2 | 11/2004 | Frigg et al. |
| 6,858,031 B2 | 2/2005 | Morrison et al. |
| 6,863,694 B1 | 3/2005 | Boyce et al. |
| 6,866,665 B2 | 3/2005 | Orbay |
| 6,893,444 B2 | 5/2005 | Orbay |
| 6,955,677 B2 | 10/2005 | Dahners |
| 6,974,461 B1 | 12/2005 | Wolter |
| 7,011,659 B2 | 3/2006 | Lewis et al. |
| 7,070,600 B2 | 7/2006 | Silverman |
| 7,077,844 B2 | 7/2006 | Michelson |
| 7,153,309 B2 | 12/2006 | Huebner et al. |
| 7,635,365 B2 | 12/2009 | Ellis et al. |
| 7,695,501 B2 | 4/2010 | Ellis et al. |
| 7,695,502 B2 | 4/2010 | Orbay et al. |
| 7,727,264 B2 | 6/2010 | Orbay et al. |
| 7,731,718 B2 | 6/2010 | Schwammberger et al. |
| 2001/0011172 A1 | 8/2001 | Orbay et al. |
| 2002/0004660 A1 | 1/2002 | Henniges et al. |
| 2002/0032446 A1 | 3/2002 | Orbay |
| 2002/0055741 A1 | 5/2002 | Schlapfer et al. |
| 2002/0128654 A1 | 9/2002 | Steger et al. |
| 2002/0143336 A1 | 10/2002 | Hearn |
| 2002/0143337 A1 | 10/2002 | Orbay et al. |
| 2002/0143338 A1 | 10/2002 | Orbay et al. |
| 2002/0147453 A1 | 10/2002 | Gambale |
| 2002/0150856 A1* | 10/2002 | Payton .............................. 433/8 |
| 2002/0151899 A1 | 10/2002 | Bailey et al. |
| 2002/0156474 A1 | 10/2002 | Wack et al. |
| 2002/0177852 A1 | 11/2002 | Chervitz et al. |
| 2002/0183752 A1 | 12/2002 | Steiner et al. |
| 2003/0040748 A1 | 2/2003 | Aikins et al. |
| 2003/0055429 A1 | 3/2003 | Ip et al. |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner et al. |
| 2004/0116930 A1 | 6/2004 | O'Driscoll et al. |
| 2004/0127901 A1 | 7/2004 | Huebner et al. |
| 2004/0127903 A1 | 7/2004 | Schlapfer et al. |
| 2004/0127904 A1 | 7/2004 | Konieczynski et al. |
| 2004/0153073 A1 | 8/2004 | Orbay |
| 2004/0186472 A1 | 9/2004 | Lewis et al. |
| 2004/0193164 A1 | 9/2004 | Orbay |
| 2004/0193165 A1 | 9/2004 | Orbay |
| 2004/0220566 A1 | 11/2004 | Bray |
| 2004/0260291 A1 | 12/2004 | Jensen |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0015089 A1 | 1/2005 | Young et al. |
| 2005/0049593 A1 | 3/2005 | Duong et al. |
| 2005/0065520 A1 | 3/2005 | Orbay |
| 2005/0065522 A1 | 3/2005 | Orbay |
| 2005/0065523 A1 | 3/2005 | Orbay |
| 2005/0065524 A1 | 3/2005 | Orbay |
| 2005/0065528 A1 | 3/2005 | Orbay |
| 2005/0070902 A1 | 3/2005 | Medoff |
| 2005/0085818 A1 | 4/2005 | Huebner |
| 2005/0085819 A1 | 4/2005 | Ellis et al. |
| 2005/0131413 A1 | 6/2005 | O'Driscoll et al. |
| 2005/0159747 A1 | 7/2005 | Orbay |
| 2005/0165395 A1 | 7/2005 | Orbay et al. |
| 2005/0165400 A1 | 7/2005 | Fernandez |
| 2005/0171544 A1 | 8/2005 | Falkner, Jr. |
| 2005/0182405 A1 | 8/2005 | Orbay et al. |
| 2005/0182406 A1 | 8/2005 | Orbay et al. |
| 2005/0187551 A1 | 8/2005 | Orbay et al. |
| 2005/0192578 A1 | 9/2005 | Horst |
| 2005/0234458 A1 | 10/2005 | Huebner |
| 2006/0085000 A1 | 4/2006 | Mohr et al. |
| 2006/0100623 A1 | 5/2006 | Pennig |
| 2006/0150986 A1 | 7/2006 | Roue et al. |
| 2007/0043367 A1 | 2/2007 | Lawrie |
| 2007/0043368 A1 | 2/2007 | Lawrie et al. |
| 2007/0083202 A1 | 4/2007 | Eli Running et al. |
| 2007/0123883 A1* | 5/2007 | Ellis et al. ....................... 606/69 |
| 2007/0185493 A1 | 8/2007 | Feibel et al. |
| 2007/0213727 A1 | 9/2007 | Bottlang et al. |
| 2009/0069812 A1 | 3/2009 | Gillard et al. |
| 2009/0118768 A1* | 5/2009 | Sixto et al. ................... 606/280 |
| 2009/0177240 A1 | 7/2009 | Perez |
| 2010/0234896 A1 | 9/2010 | Lorenz et al. |
| 2010/0274245 A1 | 10/2010 | Gonzalez-Hernandez |
| 2010/0331844 A1 | 12/2010 | Ellis et al. |
| 2011/0160730 A1 | 6/2011 | Schonhardt et al. |

FOREIGN PATENT DOCUMENTS

| | | |
|---|---|---|
| CH | 576249 A5 | 6/1976 |
| CH | 611147 A5 | 5/1979 |
| DE | 251430 A1 | 11/1975 |
| DE | 3808937 A1 | 10/1989 |
| DE | 4201531 A1 | 7/1993 |
| DE | 4343117 A1 | 6/1995 |
| EP | 0029752 B1 | 4/1983 |
| EP | 0094039 A1 | 11/1983 |
| EP | 0179695 | 4/1986 |
| EP | 0053999 B1 | 3/1987 |
| EP | 0410309 A1 | 1/1991 |
| EP | 0415837 A2 | 3/1991 |
| EP | 0362049 B1 | 5/1992 |
| EP | 0471418 B1 | 6/1995 |
| EP | 0561295 B1 | 5/1996 |
| EP | 1250892 A2 | 10/2002 |
| FR | 742618 A | 3/1933 |
| FR | 2211851 A5 | 7/1974 |
| FR | 2254298 A1 | 7/1975 |
| FR | 2367479 A1 | 5/1978 |
| FR | 2405705 A1 | 5/1979 |
| FR | 2405706 A1 | 5/1979 |
| FR | 2406429 A1 | 5/1979 |
| FR | 2416683 A1 | 9/1979 |
| FR | 2472373 A1 | 7/1981 |
| FR | 2674118 A1 | 9/1992 |
| GB | 2245498 A | 1/1992 |
| GB | 2331244 A | 5/1999 |
| GB | 2435429 A | 8/2007 |
| JP | S47-44985 | 0/1972 |
| JP | S64-032855 A | 2/1989 |
| JP | H05-146502 A | 6/1993 |
| JP | H06-3551 Y2 | 2/1994 |
| JP | 2002542875 A | 12/2002 |
| SU | 610518 A1 | 6/1978 |
| SU | 718097 A1 | 2/1980 |
| SU | 862937 A1 | 9/1981 |
| SU | 874044 A1 | 10/1981 |
| SU | 897233 A1 | 1/1982 |
| SU | 921553 A1 | 4/1982 |
| SU | 1049054 A1 | 10/1983 |
| SU | 1130332 A1 | 12/1984 |
| SU | 1192806 A1 | 11/1985 |
| SU | 1223901 A1 | 4/1986 |
| SU | 1225556 A1 | 4/1986 |
| SU | 1544406 A1 | 2/1990 |
| SU | 1630804 A1 | 2/1991 |
| SU | 1644932 A1 | 4/1991 |
| SU | 1683724 A1 | 10/1991 |
| SU | 1711859 A1 | 2/1992 |
| SU | 1734715 A1 | 5/1992 |
| WO | WO8201645 A1 | 5/1982 |
| WO | WO8702572 A1 | 5/1987 |
| WO | WO8803781 A1 | 6/1988 |
| WO | WO9505782 A1 | 3/1995 |
| WO | WO9629948 A1 | 10/1996 |

(56) References Cited

FOREIGN PATENT DOCUMENTS

| | | |
|---|---|---|
| WO | WO9747251 A1 | 12/1997 |
| WO | WO9922089 A1 | 5/1999 |
| WO | WO0121083 A1 | 3/2001 |
| WO | WO0162136 A2 | 8/2001 |
| WO | WO0203882 A2 | 1/2002 |
| WO | WO03105712 A2 | 12/2003 |
| WO | WO2007092813 A2 | 8/2007 |
| WO | WO2007109436 A2 | 9/2007 |

OTHER PUBLICATIONS

Vitallium, Bone Plates brochure, Mar. 1948.
Moore et al., "Operative stabilization of nonpenetrating chest injuries", The Journal of Thoracic and Cardiovascular Surgery, vol. 70, No. 4, pp. 619-630, 1975.
Tarazona et al., "Surgical stabilization of traumatic flail chest", pp. 521-527, 1975.
Thomas et al., "Operative stabilization for flail chest after blunt trauma", The Journal of Thoracic and Cardiovascular Surgery, vol. 75, No. 6, pp. 793-801, 1978.
Trunkey, "Chest Wall Injuries", Cerviothoracic Trauma, vol. 3. pp. 129-149, 1986.
Klein et al., "Rib Fracture Healing after Osteosynthesis with Wire Mesh Titanium and Screws: A Histological Study in Sheep", Eur Surg Res, vol. 21 pp. 347-354, 1989.
Techmedica, Inc., The Arnett-TMP* Titanium Miniplating System brochure, 1989.
Haasler, "Open Fixation of Flail Chest After Blunt Trauma", The Society of Thoracic Surgeons, pp. 993-995, 1990.
Howmedica Inc., Dupont Distal Humeral Plates brochure, 1990.
Landreneau et al., "Strut Fixation of an Extensive Flail Chest", The Society of Thoracic Surgeons, pp. 473-475, 1991.
Synthes (USA), Biological Plating: A New Concept to Foster Bone Healing, 1991.
Synthes, CMR Matrix: MatrixRIB. Stable fixation of normal and asteoporotic ribs. Techinque Guide, 1991.
Techmedica, Inc., Techmedica Bioengineers Keep Tabs on Your Needs brochure, 1991.
Ace Medical Company, Ace 4.5/5.0 mm Titanium Cannulated Screw and Reconstruction Plate System simplified fracture fixation brochure, 1992.
Ace Medical Company, Ace 4.5/5.0 mm Titanium Cannulated Screw and Reconstruction Plate System surgical technique brochure, 1992.
Beaupre et al., "A Comparison of Unicortical and Bicortical End Screw Attachment of Fracture Fixation Plates", Journal of Orthopaedic Trauma, vol. 6, No. 3, pp. 294-300, 1992.
Ace Medical Company, Ace Titanium 3.5/4.0 mm Screw and Plate System with the Ace 3.5 mm Universal Ribbon CT/MRI compatible fixation brochure, 1994.
Esser, "Treatment of Three- and Four-Part Fractures of the Proximal Humerus with a Modified Cloverleaf Plate", Journal of Orthopaedic Trauma, vol. 8, No. 1, pp. 15-22, 1994.
Amadio, "Open Reduction of Intra-Articular Fractures of the Distal Radius", Fractures of the Distal Radius, pp. 193-202, 1995.
Ducloyer, "Treatment by Plates of Anteriorly Displaced Distal Radial Fractures", Fractures of the Distal Radius, pp. 148-152, 1995.
Gesensway et al., "Design and Biomechanics of a Plate for the Distal Radius", Journal of Hand Surgery, vol. 20, No. 6, pp. 1021-1027, 1995 (abstract only provided).
Jupiter et al., "Management of Comminuted Distal Radial Fractures", Fractures of the Distal Radius, pp. 167-183, 1995.
Waldemar Link GmbH & Co., May Anatomical Bone Plates: Plates, Bone Screws and Instruments brochure, pp. 3-4 and 10-15, 1995.
Zimmer, Inc., Forte Distal Radial Plate System brochure, 1995.
Ace Medical Company, The Ace Symmetry Titanium Upper Extremity Plates new product release brochure, 1996.
Ace Medical Company, Ace Symmetry Titanium Upper Extremity Plates surgical technique brochure, 1996.
Fernandez et al., Fractures of the Distal Radius: A Practical Approach to Management, pp. 103-188, 1996.

Avanta Orthopaedics, SCS/D Distal Radius Plate System brochure, 1997.
Fitoussi et al., "Treatment of Displaced Intra-Articular Fractures of the Distal End of the Radius With Plates", The Journal of Bone and Joint Surgery, vol. 79, No. 9, pp. 1303-1312, 1997 (abstract only provided).
Synthes (USA), The Titanium Distal Radius Plate, technique guide, 1997.
TriMed Inc., TriMed Wrist Fixation System brochure, 1997.
Synthes, Small Titanium Plates overview page, p. 2a-33, Mar. 1997.
Synthes, Titanium Distal Radius Instrument and Implant Set standard contents description pages, Mar. 1997.
Ring et al., "Prospective Multicenter Trial of a Plate for Dorsal Fixation of Distal Radius Fractures", The Journal of Hand Surgery, vol. 22A, No. 5, pp. 777-784, Sep. 1997.
Avanta Orthopaedics, SCS/V Distal Radius Plate Volar brochure, 1998.
Oyarzun et al., "Use of 3.5mm Acetabular Reconstruction Plates for Internal Fixation of Flail Chest Injuries", Section of Cardiothoracic Surgery, pp. 1471-1474, 1998.
Voggenreiter et al., "Operative Chest Wall Stabilization in Flail Chest—Outcomes of Patients With or Without Pulmonary Contusion", American College of Surgeons, pp. 130-138, 1998.
Kolodziej et al., "Biomechanical Evaluation of the Schuhli Nut", Clinical Orthopaedics and Related Research, vol. 347, pp. 79-85, Feb. 1998.
Acumed Inc., Congruent Distal Radius Plate System description, Mar. 4, 1998.
Trumble et al., "Intra-Articular Fractures of the Distal Aspect of the Radius", Journal of Bone and Joint Surgery, vol. 80A, No. 4, pp. 582-600, Apr. 1998.
Kambouroglou etal., "Complications of the AO/ASIF Titanium Distal Radius Plate System ($\pi$ Plate) in Internal Fixation of the Distal Radius: A Brief Report", Journal of Hand Surgery, vol. 23A, No. 4, pp. 737-741, Jul. 1998.
DePuy Ace, TiMAX Pe.R.I. Small Fragment Upper Extremity description pages, 1999.
Palmer etal., "The Use of Interlocked 'Customised' Blade Plates in the Treatment of Metaphyseal Fractures in Patients with Poor Bone Stock", Injury, Int. J. Care Injured, vol. 31, pp. 187-191, 1999.
Synthes (USA), The Distal Radius Plate Instrument and Implant Set technique guide, 1999.
Tatsumi et al., "Bioabsorable Poly-L-Lactide Costal Coaptation Pins and Their Clinical Application in Thoroacotomy", Original Articles: General Thoracic. pp. 765-768, 1999.
Morgan et al., "Salvage of Tibial Pilon Fractures Using Fusion of the Ankle with a 90° Cannulated Blade Plate: A Preliminary Report", Foot & Ankle International, vol. 20, No. 6, pp. 375-378, Jun. 1999.
Nunley et al., "Delayed Rupture of the Flexor Pollicis Longus Tendon After Inappropriate Placement of the $\pi$ Plate on the Volar Surface of the Distal Radius", Journal of Hand Surgery, vol. 24, No. 6, pp. 1279-1280, Nov. 1999.
Toby, Scaphoid Protocols Using the Acutrak® Bone Screw System brochure, published by Acumed, Inc., Dec. 7, 1999.
Biomet Orthopedics, Inc., Supracondylar Cable Plate brochure, 2000.
Cacchione et al., "Painful Nonunion of Multiple Rib Fractures Managed by Operative Stabilization", The Journal of Trauma, Injury, Infection and Critical Care, vol. 48, No. 2, pp. 319-321, 2000.
Peine et al., "Comparison of Three Different Plating Techniques for the Dorsum of the Distal Radius: A Biomechanical Study", Journal of Hand Surgery, vol. 25A, No. 1, pp. 29-33, Jan. 2000.
Young, "Outcome Following Nonoperative Treatment of Displaced Distal Radius Fractures in Low-Demand Patients Older Than 60 Years", Journal of Hand Surgery, vol. 25A, No. 1, pp. 19-28, Jan. 2000.
Putnam et al., "Distal Radial Metaphyseal Forces in an Extrinsic Grip Model: Implications for Postfracture Rehabilitation", Journal of Hand Surgery, vol. 25A, No. 3, pp. 469-475, May 2000.
Surfix Technologies, Single Units Osteosynthesis brochure, Sep. 2000.

(56) References Cited

OTHER PUBLICATIONS

Lardinois et al., "Pulmonary Function Testing After Operative Stabilisation of the Chest Wall for Flail Chest", European Journal of Cardio-thoracic Surgery (2001) 20:496-501.
Ng et al., "Operative Stabilisation of Painful Non-united Multiple Rib Fractures", Injury (2001) 32:637-639.
Synthes (USA), Titanium Distal Radius Plates description page, 2001.
Wright Medical Technology, Inc., Locon-T Distal Radius Plating System case study and surgical method, 2001.
TriMed Inc., TriMed Wrist Fixation System internet description pages, 2001.
Slater et al., "Operative Stabilization of Flail Chest Six Years After Injury", Annals of Thoracic Surgery (2001) Aug. 600-601.
Sanchez-Sotelo et al., "Principle-Based Internal Fixation of Distal Humerus Fractures, Techniques in Hand & Upper Extremity Surgery", vol. 5, No. 4, pp. 179-187, Dec. 2001.
Abel et al., "An Axially Mobile Plate for Fracture Fixation", Internal Fixation in Osteoporotic Bone, pp. 279-283, 2002.
An, Y.H., Internal Fixation in Osteoporotic Bone, pp. 82-83, 2002.
Konrath et al., "Open Reduction and Internal Fixation of Unstable Distal Radius Fractures: Results Using the Trimed Fixation System", Journal of Orthopaedic Trauma, vol. 16, No. 8, pp. 578-585, 2002.
Mizuho Co., Ltd., Jplate Diaphysis Plates for Japanese brochure, 2002.
Synthes (USA), 3.5 mm LCP™ Proximal Humerus Plate technique guide, 2002.
Tanaka et al., "Surgical Stabilization or Internal Pneumatic Stabilization? A Prospective Randomized Study of Management of Severe Flail Chest Patients", Journal of Trauma (2002) 52:727-732.
Sing et al., "Thoracoscopic Resection of Painful Multiple Rib Fractures: Case Report" The Journal of Trauma, vol. 52, No. 2, pp. 391-392, 2002.
Tornetta, Distal Radius Fracture, Journal of Orthopaedic Trauma, vol. 16, No. 8, pp. 608-611, 2002.
Wright Medical Technology, Inc., Locon-T Distal Radius Plating System brochure, 2002.
Zimmer, Inc., Periarticular Plating System brochure, 2002.
Acumed Inc., Congruent Plate System—The Mayo Clinic Congruent Elbow Plates brochure, May 7, 2002.
Acumed Inc., Modular Hand System brochure, Aug. 2002.
Acumed Inc., Modular Hand System brochure, Sep. 2002.
Harvey et al., "The Use of a Locking Custom Contoured Blade Plate for Peri-Nonunions", Injury, Int. J. Care Injured, vol. 34, pp. 111-116, 2003.
Chin et al., "Salvage of Distal Tibia Metaphyseal Nonunions With the 90° Cannulated Blade Plate", Clinical Orthopaedics and Related Research, No. 409, pp. 241-249, 2003.
Hooker et al., Fixation of Unstable Fractures of the Volar Rim of the Distal Radius with a Volar Buttress Pine®, 2003.
Rozental et al., Functional Outcome and Complications Following Two Types of Dorsal Plating for Unstable Fractures of the Distal Part of the Radius, Journal of Bone and Joing Surgery, vol. 85, No. 10, pp. 1956-1960, 2003 (abstract only).
Osada et al.., "Comparison of Different Distal Radius Dorsal and Volar Fracture Fixation Plates: A Biomechanical Study", Journal of Hand Surgery, vol. 28A, No. 1, pp. 94-104, Jan. 2003.

Turner et al., Tendon Function and Morphology Related to Material and Design of Plates for Distal Radius Fracture Fixation: Canine Forelimb Model, Orthopaedic Research Society, Feb. 2003.
Erothitan Titanimplantate AG, Titanium Wire Plate Osteosynthesis System According to Dr. Gahr internet printout, print date Feb. 6, 2003.
Simic, "Fractures of the Distal Aspect of the Radius: Changes in Treatment Over the Past Two Decades", Journal of Bone and Joint Surgery, vol. 85-A, No. 3, pp. 552-564, Mar. 2003.
Leung et al., "Palmar Plate Fixation of AO Type C2 Fracture of Distal Radius Using a Locking Compression Plate—A Biomechanical Study in a Cadaveric Model", Journal of Hand Surgery, vol. 28B, No. 3, pp. 263-266, Jun. 2003.
Martin GmbH & Co. KG, Bilder Internet printout, print date Sep. 5, 2003.
Mayberry, "Absorbable Plates for Rib Fracture Repair: Preliminary Experience", Journal of Trauma Injury, Infection and Critical Care. vol. 55, No. 5, pp. 835-839, Nov. 2003.
Moore et al., Clinically Oriented Anatomy, Fourth Edition, pp. 70-71, 2004.
Orthocopia, LLC, Synthes Volar Distal Radius Locking Plate Internet description page, 2004.
Ruch et al., "Results of Palmar Plating of the Lunate Facet Combined with External Fixation for the Treatment of High-Energy Compression Fractures of the Distal Radius", J. Orthop. Trauma, Vo. 18, No. 1, pp. 28-33, Jan. 2004.
Sanatmetal, Rib Securing Clamped Plate, internet printout, Sep. 2004 <http://www.sanatmetal.hu/catalog/pict/1_5_89a_1.jpg>.
Zespol Bone Plates, in Mikromed—Catalogue 2004 (Nov. 2004), original website <http://www.mikromed.pl/katalog/Main/main_eng.htm> and < http://www.mikromed.pl/katalog/zespol_eng/plytki.htm >, viewable via the Internet Archive Wayback Machine < http://replay.waybackmachine.org/ 20070830023439/http://www.mikromed.pl/katalog/zespol_eng/plytki.htm >.
Zespol Bone Screws, in Mikromed—Catalogue 2004 (Nov. 2004), original website <http://www.mikromed.p1/katalog/Main/main_eng.htm> and < http://www.mikromed.pl/katalog/zespol_eng/wkrety.htm >, viewable via the Internet Archive Wayback Machine < http://replay.waybackmachine.org/ 20050226124226/http://www.mikromed.pl/katalog/zespol_eng/wkrety.htm >.
DVO Extremity Solutions, Mlfx Dorsal IM Plate, brochure, Sep. 2005.
Stryker SmartLock Locking Screw Technology, advertisement, The Journal of Hand Surgery, vol. 30A, No. 1, Jan. 2005.
Legacy Biomechanics Laboratory, Applied Research, Jan. 2006, original website <http://www.biomechresearch.org/sling.html>, viewable via the Internet Archive Wayback Machine <http://replay.waybackmachine.org/ 20060320091922/http://www.biomechresearch.org/sling.html>.
Osteomed, images of Resorable Plates, Feb. 2006 <http://www.osteomedcorp.com/images/library/resorbfixation.gif>.
AO Foundation, TK System: Innovations, Dec. 2011.
US Receiving Office of WIPO, International Search Report and Written Opinion of the International Searching Authority regarding PCT Patent Application No. PCT/US2013/023476, dated Mar. 22, 2013, 22 pages.

* cited by examiner

CLIP FOR RIB STABILIZATION

CROSS-REFERENCE TO PRIORITY APPLICATIONS

This application is based upon and claims the benefit under 35 U.S.C. §119(e) of U.S. Provisional Patent Application Ser. No. 61/590,955, filed Jan. 26, 2012, which is incorporated herein by reference in its entirety for all purposes.

CROSS-REFERENCE TO OTHER MATERIAL

The following patent is incorporated herein by reference in its entirety for all purposes: U.S. Pat. No. 7,695,501, issued Apr. 13, 2010.

INTRODUCTION

The rib cage, or thoracic cage, is composed of bone and cartilage that surround the chest cavity and organs therein, such as the heart and the lungs. In humans, the rib cage typically consists of 24 ribs (interchangeably termed rib bones), twelve thoracic vertebrae, the sternum (or breastbone), and the costal cartilages. The ribs articulate with the thoracic vertebrae posteriorly and, with the exception of the bottom two pairs of ribs (the floating ribs), are connected to the sternum anteriorly using the costal cartilages.

One or more ribs may need to be stabilized temporarily after a thoracotomy, which is a surgical incision through the chest wall to provide access to the chest cavity. For example, a rib may sustain an iatrogenic fracture, that is, a fracture induced inadvertently by a surgeon. More particularly, a rib may be fractured by a surgeon when the thoracic cage is deformed to create an entry site to the chest cavity by spreading ribs and/or urging apart the halves of a cut sternum. In other cases, a surgeon may choose to perform an osteotomy by placing a cut through one or more ribs to provide better access to the chest cavity and/or to relieve pressure on the ribs. In any event, the chest cavity may be accessed medially (through the sternum), posterolaterally (between ribs in a back region of the chest wall), anterolaterally (between ribs in a front region of the chest wall), or the like, and one or more ribs near any of these positions may be fractured or cut during surgery.

Implants have been developed for rib fixation in trauma patients, particularly to treat flail chest produced by fracture of multiple adjacent ribs. However, such implants may not be necessary or desirable when only one or two ribs need to be stabilized, particularly when rib stabilization is only an ancillary procedure to be performed during a surgery.

Therefore, a rib stabilization system is needed for surgically-created rib discontinuities.

SUMMARY

The present disclosure provides a system, including methods, apparatus, and kits, for rib stabilization. The system may comprise a clip member having a bridge region and a pair of leaf portions connected to each other by the bridge region. The clip member may be configured to be placed on a rib bone with the leaf portions disposed on opposite sides of the rib bone. The system also may comprise a securing member, such as a suture, to attach the clip member to the rib bone, with the securing member extending at least twice between the leaf portions.

DETAILED DESCRIPTION

Figure 1:
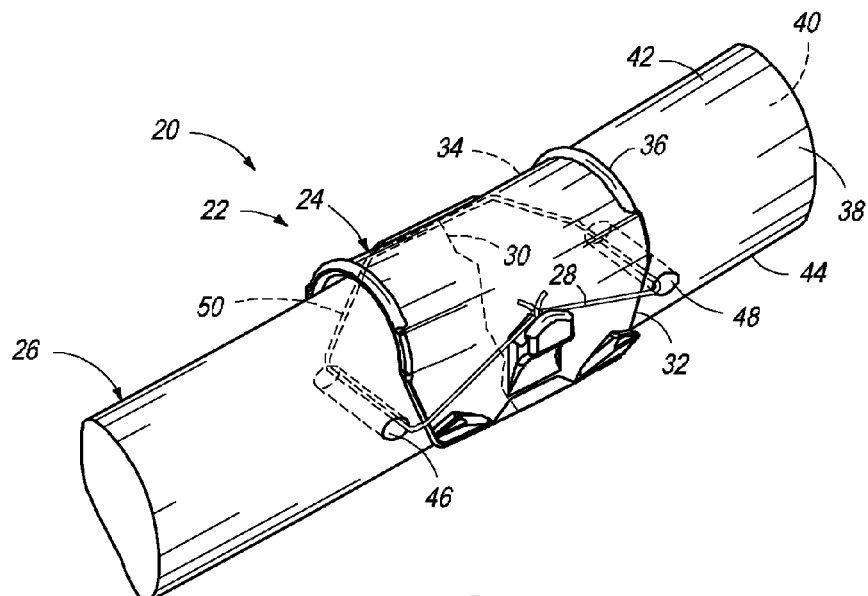
FIG. 1 is a view of selected aspects of an exemplary rib stabilization system including a clip member disposed on a fractured rib bone and attached with a securing member (e.g., a suture loop), in accordance with aspects of the present disclosure.

The present disclosure provides a system, including methods, apparatus, and kits, for rib stabilization. The system may comprise a clip member having a bridge region and a pair of leaf portions connected to each other by the bridge region. The clip member may be configured to be placed on a rib bone with the leaf portions disposed on opposite sides of the rib bone. The system also may comprise a securing member, such as a suture, to attach the clip member to the rib bone, with the securing member extending at least twice between the leaf portions.

An exemplary method of rib stabilization is provided. In the method, a clip member may be selected. The clip member may have a bridge region and a pair of leaf portions (e.g., a proximal leaf portion and a distal leaf portion) connected to each other by the bridge region. For example, the clip member may be U-shaped. The clip member may be disposed on a rib bone, with the leaf portions disposed on opposite sides of the rib bone. The clip member may (or may not) span a discontinuity of the rib bone. The clip member may be attached to the rib bone with a securing member, such as a suture, that extends between the leaf portions at least twice (e.g., exactly twice), and through the rib bone at least twice (e.g., exactly twice). The securing member may (or may not) span a discontinuity of the rib bone. In some embodiments, the securing member may be hooked onto a bracket of the clip member to tighten the securing member. In some embodiments, the securing member may extend along the rib bone through a retainer of the distal leaf portion. In some embodiments, the clip member may include at least one or a pair of integral drill guides that are detached from the proximal leaf portion after holes are formed through the rib bone along axes defined by the drill guide(s). In some embodiments, the securing member may be centered around an axis that extends through the bridge region, such as orthogonally through the bridge region.

An exemplary system for rib stabilization is provided. The system may comprise a clip member having a bridge region and a proximal leaf portion and a distal leaf portion connected to each other by the bridge region. The clip member may be configured to be placed on a rib bone with the leaf portions disposed on opposite sides of the rib bone. The system also may comprise a securing member to attach the clip member to the rib bone, with the securing member including a suture. The clip member may, for example, have any combination of a bracket to engage the suture (e.g., with the bracket configured to permit the suture to be hooked onto the bracket to tighten the securing member), a retainer provided by the distal leaf portion to hold the suture, and/or integral drill guides that are detachable after use, among others.

The rib stabilization system disclosed herein may have substantial advantages over other approaches to rib repair. The advantages may include any combination of the following: faster and easier installation, better conformability of the implant to a rib bone, bioresorbability, less stress shielding of the rib bone (to produce more rapid healing), and/or adjustable axial compression of the rib bone, among others.

These and other aspects of the present disclosure are described in the following sections: (I) exemplary rib stabilization system, (II) methods of rib stabilization, (III) exemplary system combinations, and (IV) examples.

I. Exemplary Rib Stabilization System

This section describes an exemplary rib stabilization system 20; see FIGS. 1-8. The system may include a stabilizing implant or device 22 comprising at least one clip member 24. The clip member (and/or implant/device) may be attached to a rib bone 26 with a securing member 28 that includes a suture, with the clip member (and/or implant/device) spanning a discontinuity 30, such as a fracture or cut, in the rib bone. (The clip member interchangeably may be termed a clip, a plate, an implant, and/or a device.)

Clip 24 may have a pair of leaf portions 32, 34 connected to each other by a bridge region 36. Each leaf portion interchangeably may be termed a mounting portion and/or a clip region, and may include a plate region. When the clip is disposed on rib bone 26, the leaf portions may be disposed on opposite sides 38, 40 of the rib bone, to opposingly flank the rib bone. Proximal leaf portion 32 (interchangeably termed the front region of the clip) may be positioned adjacent outer side 38 of the rib bone and adjacent/against an outer surface region thereof (i.e., relatively closer to the surgeon and/or the exterior of the recipient of the clip (the subject/patient)). Distal leaf portion 34 (interchangeably termed the back or rear region of the clip) may be positioned on inner side 40 of the rib bone and adjacent/against an inner surface region thereof (i.e., relatively farther from the surgeon and/or the exterior of the recipient of the clip and relatively closer to (or in) the chest cavity). The outer and inner surface regions of the rib bone may be anterior, lateral, or posterior surface regions, among others, of a rib bone and/or rib cage. The leaf portions may face each other and may be separated by a receiving space for a rib bone. The leaf portions may project the same or different distances from the bridge region to form a U-shaped structure. For example, proximal leaf portion 32 can project farther from the bridge region than the distal leaf portion, to extend to a more caudal/inferior position on the rib bone. Each leaf portion may or may not project past the inferior/caudal boundary of the rib bone.

Bridge region 36 may be disposed on a superior (or rostral) side 42 of the rib bone, adjacent/against a superior/rostral surface region thereof that extends between the outer surface region and the inner surface region of the rib bone. Alternatively, the clip may be installed in an inverted configuration, with bridge region 36 disposed on an inferior (or caudal) side 44 of rib bone 26, adjacent/against an inferior/caudal surface region thereof that extends between an outer surface region and an inner surface region of the rib bone. Accordingly, the bridge region may be described as a top region (or a bottom region) of the clip.

Securing member 28 may extend at least twice between proximal leaf portion 32 and distal leaf portion 34. The securing member may extend twice between the leaf portions on a pair of separate paths through rib bone 26, namely, through each of a pair of holes 46, 48 formed in rib bone 26. Each hole may be a bore or through-hole that extends from outer side 38 to inner side 40 of rib bone 26. The holes may be spaced longitudinally along rib bone 26 from each other, and may be formed on respective opposite sides of rib discontinuity 30, or may be formed on the same side of a rib discontinuity (see Example 2).

Securing member 28, alone or in combination with clip 24, may form a loop 50. The loop may be centered around an axis 52 (interchangeably termed a receiving axis) that extends through the bridge region and through rostral/superior and caudal/inferior surface regions of the rib bone (see FIG. 6). For example, to form a complete circuit, the loop may extend on inner side 40, generally axially along the rib bone and over/through distal leaf portion 34, to hole 46, then through hole 46 to outer side 38, next generally axially along the rib bone on outer side 38 and over proximal leaf portion 32, to hole 48, then through hole 48, and back to distal leaf portion 34. The securing member thus may attach the clip to the rib bone without traversing the superior or inferior sides of the rib bone outside bone.

The securing member may include one or more pieces/lengths of suture (i.e., a surgical thread, string, cord, wire, cable, etc.). In other words, the suture may be any long, flexible piece(s) of material capable of extending along various nonlinear paths, such a path extending at least twice through a rib bone. The suture may be formed of natural and/or artificial materials, such as a bioresorbable or non-resorbable polymer (e.g., plastic), metal, or the like. Each piece/length of suture may be composed of a single fiber/filament or a bundle of two or more fibers/filaments. Exemplary securing members may include a single length/piece of suture (or a pair of lengths/pieces of suture) having a pair of free ends 54 that can be fastened to each other (see FIGS. 5 and 6). The ends can be fastened to each other by tying the ends together to form a knot, twisting the ends together, engagement of the ends with a separate suture-locking device (e.g., a suture clamp, a crimp block, etc.), or the like. In some cases, the securing member may be integrally attached to the clip member, such as by over-molding the clip member around a region(s) of a pre-formed securing member, forming the securing member as a continuous extension of the clip member, or the like.

Figure 7:
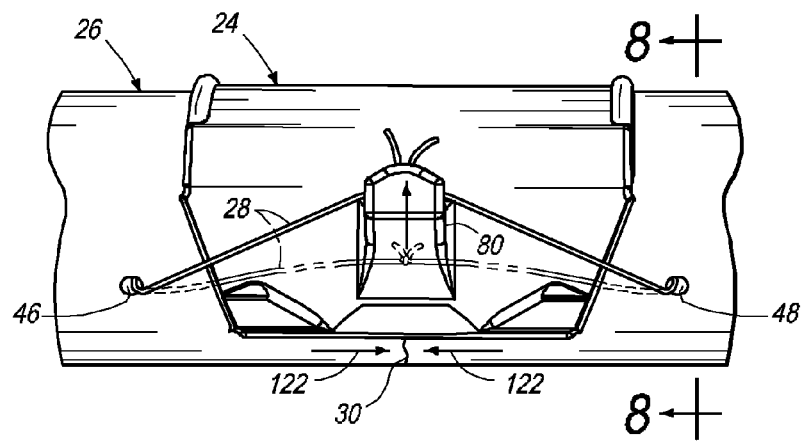
FIG. 7 is a front elevation view of the rib stabilization system of FIG. 1 illustrating how the securing member can be hooked onto a hitching bracket of the clip member to tighten the securing member and compress the rib bone axially, in accordance with aspects of the present disclosure.
Figure 8:
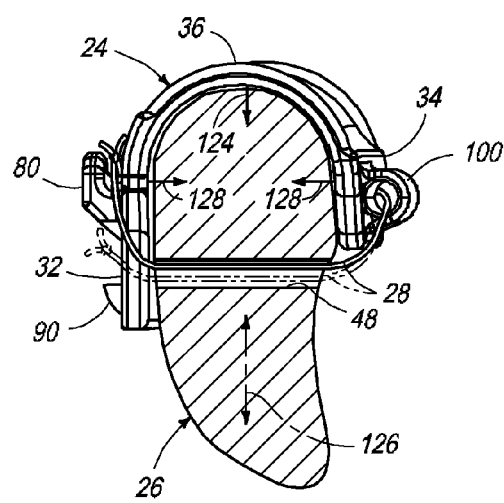
FIG. 8 is end view of the rib stabilization system of FIG. 1, taken generally along line 8-8 of FIG. 7 through the rib bone.

FIGS. 2-6 show a larger form of clip 24 having a central body region 60 and a pair of integral drill guides 62, 64 (interchangeably termed guide regions). (FIGS. 1, 7, and 8 show a smaller form of the clip lacking the guides.) Each drill guide may define a guide axis 66 along which the tip of a hole-forming tool (a drill), such as a rotary drill or a percussive drill, may be advanced to create one of holes 46, 48 (see FIGS. 1 and 2).

Figure 2:
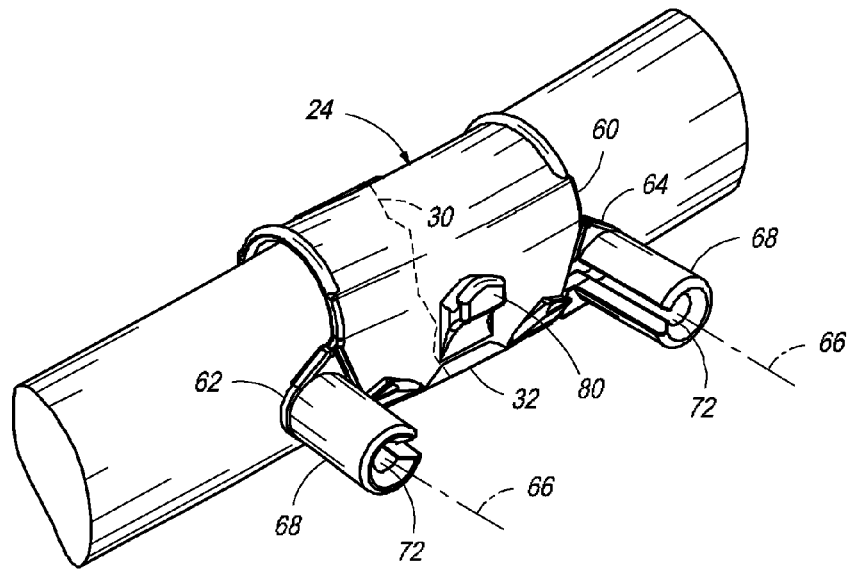
FIG. 2 is a view of the rib stabilization system of FIG. 1, taken generally as in FIG. 1 but in the absence of the securing member and with the clip member present on the rib bone as a larger form, before detachment of a pair of integral drill guides from the clip member to produce the smaller form shown in FIG. 1, in accordance with aspects of the present disclosure.
Figure 3:
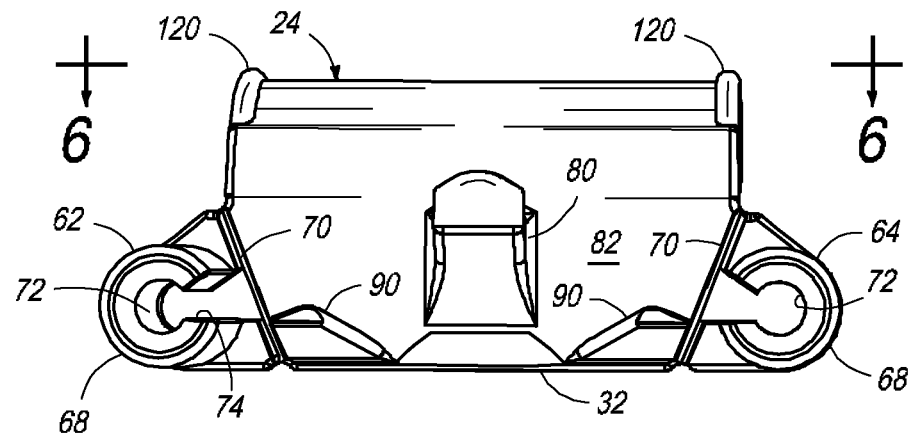
FIG. 3 is a front elevation view of the clip member of FIG. 2.

Each drill guide may project laterally from an edge of body region 60 and/or proximal leaf portion 32 of the clip to form a protrusion 68 on an outer surface region of the clip (see FIGS. 2 and 3). The protrusion may be cylindrical. Each drill guide may (or may not) be detachably connected to body region 60 of the clip via proximal leaf portion 32. The drill guide may be continuous with body region 60 of the clip. For example, clip 24 may form a frangible site 70 connecting each drill guide to the proximal leaf portion (see FIGS. 3 and 4), which allows the drill guide to be broken off of the clip after use. The frangible site may, for example, be a groove, opposing grooves formed in inner and outer surface regions of the clip, and/or a set of perforations, among other others, that allow each drill guide to be removed from the clip (e.g., snapped off) after formation of a corresponding hole 46 or 48, and before a surgical incision is closed over the clip. In other embodiments, each drill guide may be provided by a discrete guide piece that is attached to a body piece of the clip.

Each drill guide may define an aperture 72 that is coaxial with guide axis 66 (see FIGS. 2 and 3). The aperture may be elongated parallel to guide axis 66, such that guides 62 and 64 project away from the rib bone (see FIG. 2), in a direction transverse to a plane defined by a plate region of proximal leaf portion 32, and much farther than the average thickness of the proximal leaf portion. Aperture 72 may be open not only at both ends but also along a lateral side thereof. For example, each guide may define an axial slot 74 (interchangeably termed a suture slot) formed in a wall of protrusion 68 and contiguous with aperture 72 (see FIG. 3). Slot 74 may be bounded by a lateral edge of proximal leaf portion 32 at the base of the guide, which allows securing member 28 to be threaded axially through aperture 72, and then removed from the aperture/guide, at a suitable time, by lateral motion of the securing member and/or guide. Guides 62 and 64 may be slotted so that securing member 28 is temporarily held in place while the surgeon passes the securing member from inward of the rib bone to outward of the rib bone. The guides then can be snapped off once the securing member has been passed and, optionally, tied. The guides can ensure proper location and depth of holes 46, 48. For example, each guide can function as a stop to prevent a drill from being advanced too far past the inner surface region of the rib bone.

FIGS. 2, 3, and 5-8 show additional projections that may be formed on the front side of clip 24. The clip may have a hitching bracket 80 that projects from an outer surface region 82 of proximal leaf portion 32. (Bracket 80 interchangeably may be termed a receiver, a hitching post, or a peg.) Bracket 80 may form a lip 84 that projects upwards in a spaced relation from a plate region of proximal leaf portion 32 to create a recess 88 (interchangeably termed a slot) between the lip and the plate region (see FIG. 5). Securing member 28 can be hooked onto bracket 80 by urging the securing member over lip 84 and into recess 88, to increase tension on (i.e., tighten) the securing member (also see FIGS. 7 and 8). The clip also may have a pair of ridges 90 (interchangeably termed suture guide ridges) formed on outer surface region 82 adjacent respective guides 62, 64 (see FIGS. 3, 6, and 8). The ridges may support end regions of securing member 28 during installation and may direct the end regions centrally on the proximal leaf portion, to help to ensure that the securing member is in the correct place during installation. Also, ridges 90 may restrict the clip from twisting about the long axis of the rib bone by engaging the securing member to prevent the securing member from slipping to a position below the ridges (e.g., caudal to the proximal leaf portion on the rib bone).

Figure 4:
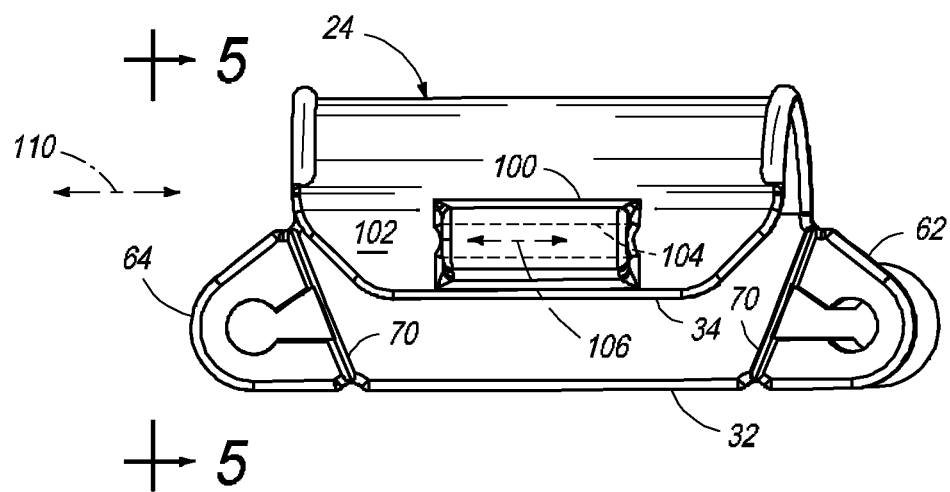
FIG. 4 is a back elevation view of the clip member of FIG. 2.
Figure 5:
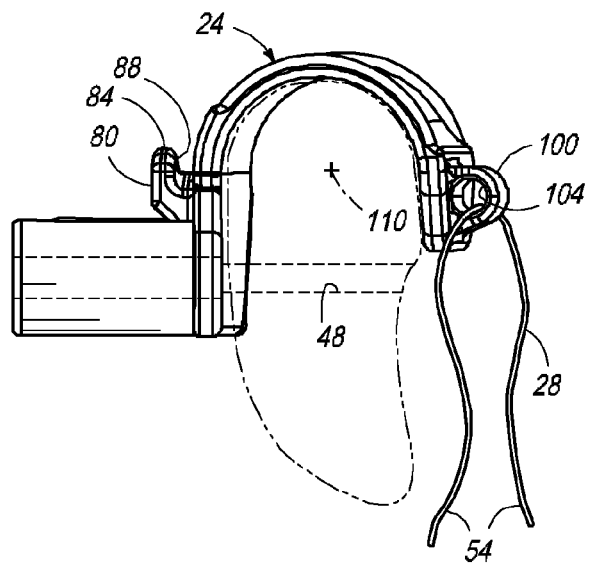
FIG. 5 is an end view (a right side view) of the clip member of FIG. 2, taken generally along line 5-5 of FIG. 4 and with the securing member of FIG. 1 preloaded in the clip member, before the free ends of the securing member are tied together.
Figure 6:
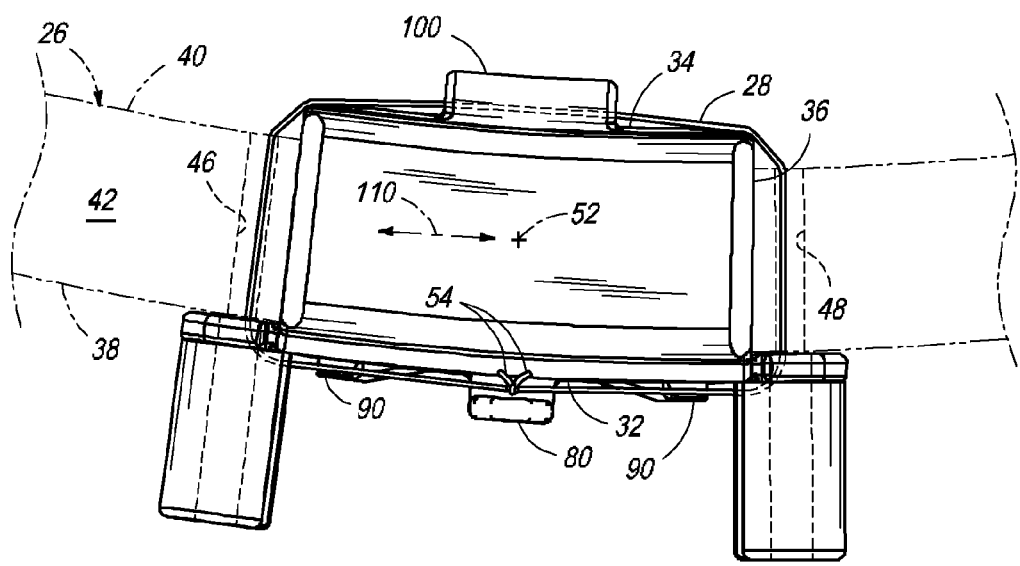
FIG. 6 is a top view of the clip member of FIG. 2, taken after installation of the securing member as in FIG. 1.

FIGS. 4, 5, and 6 show a retainer 100 formed by distal leaf portion 34. The retainer may project from an outer surface region 102 of a plate region of distal leaf portion 34, and may have a tubular structure. The retainer may form an opening, such as a channel 104, to receive and hold securing member 28. The channel may define an axis 106 that extends parallel to a local long axis of rib bone 26, and parallel to a through-axis 110 defined by clip 24. Through-axis 110 is at least generally parallel to, and at least generally equidistant from the leaf portions and the bridge region of the clip. Securing member 28 may be pre-loaded into retainer 100 before the clip is disposed on rib bone 26 (see FIG. 5).

FIG. 3 shows further aspects of the clip's geometry. The clip may be made flexible by a relatively thinner bridge region, which may be stiffened by one or more rib members 120 (interchangeably termed stiffening ribs). The rib members may be formed on an outer (or inner) surface region of the bridge region. The average thickness of the bridge region may be less than the average thickness of the plate regions of one or both leaf portions, as measured between the outer and inner surface regions of the clip. In some cases, the bridge region may have an average thickness that is no more than about 75% or 50% of the average thickness of the plate regions of the leaf portions.

FIGS. 7 and 8 illustrate the forces generated by the tension of securing member 28. The tension may be created and/or increased by fastening the free ends of the securing member to each other and/or by hooking the fastened securing member onto bracket 80. In these views, securing member 28 is shown in phantom outline for a less-tensioned configuration, before being hooked onto bracket 80, and with solid lines for a more-tensioned configuration that removes any slack in the fastened securing member, after being hooked onto bracket 80. Tension on the securing member may apply compressive force to rib bone 26 longitudinally between holes 46, 48, indicated by arrows at 122 (see FIG. 7). Also, tension on the securing member may apply rostral-caudal force, indicated by an arrow at 124, that urges bridge region 36 toward rib bone 26 (and clip member 24 is urged caudally/inferiorly on the rib bone) (see FIG. 8). Rostral-caudal forces may be generated with the securing member by positioning holes 46, 48 more caudally/inferiorly along rostral-caudal axis 126 than bracket 80 and retainer 100 (see FIG. 8) (and/or farther from bridge region 36 than the bracket and retainer. Further, the tensioned securing member may apply compressive force on leaf portions 32, 34, indicated by force arrows at 128, to urge the leaf portions toward each other (and toward respective, adjacent outer or inner surface regions of rib bone 26).

Hooking the suture loop onto the hitching bracket may apply compressive forces to the rib bone and/or clip along three generally orthogonal axes. The compressive forces may include axial compression of the rib bone at the fracture or cut in the rib bone. Also, the compressive forces may urge the proximal and distal leaf portions of the clip toward each other against the rib bone and may create a downward force pulling the bridge region to the rib bone, thereby pulling the clip tight to the rib bone on three sides.

The clip may have features focused on making installation easy, repeatable, and stable. The features may include a general "U" shape in one or more lengths and widths that may be contoured further, such as by thermoforming, to fit a variety of rib shapes and sizes (e.g., thicknesses).

The clip and securing member of the present disclosure may be formed of any suitable biologically compatible material, such as metal, plastic, or the like. In exemplary embodiments, the clip is molded of plastic (e.g., from a bioresorbable polymer), and both the clip and the securing member are bioresorbable. (The terms "bioresorbable" and "bioabsorbable" are interchangeable.) Further aspects of rib stabilization and of clip members and securing members that may be suitable are described elsewhere in the present disclosure, such as in Sections II and IV, and in the references identified above under Cross-References, which are incorporated herein by reference, namely, U.S. Provisional Patent Application Ser. No. 61/590,955, filed Jan. 26, 2012; and U.S. Pat. No. 7,695,501, issued Apr. 13, 2010.

II. Methods of Rib Stabilization

This section describes exemplary methods of rib stabilization with a device or implant that includes at least one clip attached to bone with a flexible securing member (e.g., a suture). The steps described in this section may be performed in any suitable order and combination and with any of the apparatus, features, or approaches described elsewhere in the present disclosure.

A rib bone to be stabilized may be selected. The rib bone may have at least one discontinuity, such as a fracture or cut, among others. The discontinuity may be located at any suitable position along the selected rib bone, such as a medial, anterior, lateral, or posterior position of a rib cage that includes the rib bone. In some cases, the fracture or cut may be produced during a surgical procedure, either deliberately or inadvertently by a surgeon. The discontinuity may be produced and stabilized during the same surgical operation.

An implantable device for rib stabilization may be selected. The device may include one or more clip members. The clip may be a selected from a set of clips having different sizes/shapes (i.e., different separation distances between the leaf portions, different lengths/widths of leaf portions, different radii of curvature for the bridge region, etc.). In some cases, different clips can be connected together on a multilimbed (e.g., Y-shaped) bar that may be used by the surgeon as a sizer. Once the correct size is determined the surgeon can snap the clip at the connection point located at the base of the clip, removing the clip from the sizer. The remaining clips and sizer may be discarded or used on another fracture/cut within the same case (i.e., on the same subject during the same surgery).

The selected clip is prepared for installation. The surgeon may prep the clip for installation by selecting suture and feeding the suture through a retainer, such as a suture channel, located in the back of the clip, or the clip may be supplied pre-loaded with suture.

The clip also may be thermoformed intraoperatively to provide a better fit to the rib bone. Heating the clip may be performed off the rib bone, such as in a bath or oven, or on the rib bone, such as with a heat pack or heat gun, to render the clip more conformable. The clip may be composed of a polymer having a relatively low glass transition temperature (e.g., less than about 75° C. or 65° C., among others). The clip (or a region thereof) may be heated above the glass transition temperature, and then the heated clip may be reshaped, for example, compressed (or expanded) to urge the leaf portions closer together (or farther apart). The clip may be reshaped off or on the rib bone. In exemplary embodiments, the clip may be composed of polylactic acid, which has a glass transition temperature of about 60° C.

The clip loaded with a length of suture may be positioned on the rib bone with the discontinuity generally centered between the left and right ends of the clip. The suture ends may be kept on the front side of the rib (e.g., adjacent the proximal leaf portion of the clip). A clamp and/or a surgical assistant may hold the clip in place while the surgeon drills a pair of holes through the rib bone. The holes may be drilled through apertures (such as elongated apertures or slots) defined by the clip, for example, along guide axes defined by integral drill guides. Alternatively, the holes may be drilled at positions outside the clip's footprint, such as lateral to the proximal leaf portion on opposing sides thereof. The holes may be positioned more inferiorly/caudally, and/or farther from the bridge region, than bracket 80 and/or retainer 100.

After the holes are drilled in the rib bone, a suture passer/retriever may be used to pass (e.g., pull) an end region of the suture through each hole. A suture end region disposed adjacent each end of the suture retainer of the clip may be passed through a corresponding hole in the rib bone. Each suture end region may be pulled from inward of the rib bone to outward of the rib (i.e., from the inner side to the outer side of the rib bone).

After both ends of the suture are passed through respective holes in the rib bone, the surgeon may tie the ends of the suture together to form a loop. The loop may create compression at the rib discontinuity and flex the clip such that the leaf portions are pulled together, and tight against the rib bone. The surgeon then can tighten the suture (and the stability of the rib and clip) by pulling an outer portion of the suture loop upward in front of the clip and hooking the suture loop onto the hitching bracket of the clip, where the suture can rest in the slot formed by the bracket.

If the selected clip has removable drill guides, the guides can be removed at any suitable time. In any event, with the suture tied and elevated into the slot of the hitching bracket, the stability of the discontinuity may be optimized. The suture may create axial compression of the rib at the discontinuity, may pull the clip downward from the front and the back, bringing the top of the clip tight against the rib. The clip may be squeezed from the front and back, bringing the front and back of the clip tight against the outer and inner rib surface regions.

Further aspects of rib stabilization are described elsewhere in the present disclosure and in the references identified above under Cross-References, which are incorporated herein by reference, namely, U.S. Provisional Patent Application Ser. No. 61/590,955, filed Jan. 26, 2012; and U.S. Pat. No. 7,695, 501, issued Apr. 13, 2010.

III. Exemplary System Combinations

The apparatus disclosed herein may be utilized and/or grouped in any suitable manner to provide a system, which may be supplied as a kit. The system (or kit) may include one or more clip members and one or more securing members. The system also or alternatively may include any combination of the following: a drill to form holes in bone, one or more clamps to engage and hold the clip members during installation, a suture passer/retriever, and instructions for use. Each system component may be configured for single use (e.g., clip members and securing members) or for multiple use (e.g., the drill, clamps, and/or suture/retriever). Some or all of the components of each system (or kit) may be provided in a sterile condition, such as packaged in a sterile container.

IV. EXAMPLES

The following examples describe selected aspects and embodiments of the present disclosure related to implants for rib stabilization. These examples are included for illustration and are not intended to limit or define the entire scope of the present disclosure.

Example 1

Clip Member with Longer Bridge Region

Figure 9:
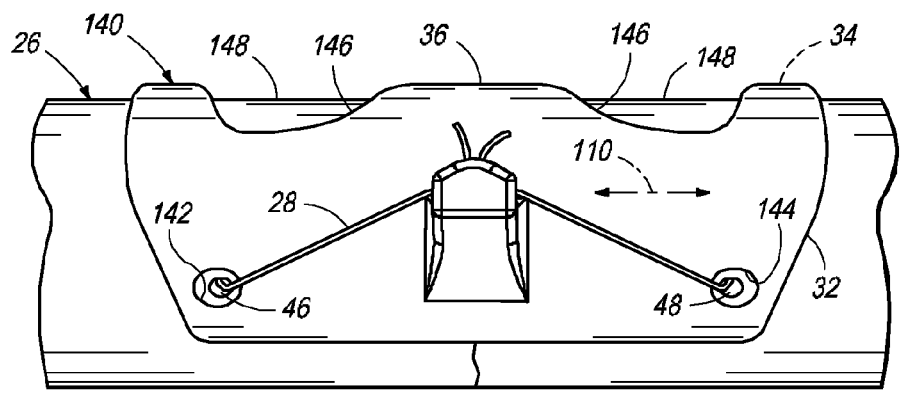
FIG. 9 is a front elevation view of selected aspects of another exemplary rib stabilization system including another exemplary embodiment of a clip member disposed on a fractured rib bone and attached with a securing member, in accordance with aspects of the present disclosure.

This example describes an exemplary clip member 140 having a bridge region 36 that has a greater characteristic dimension, measured along rib bone 26, than a loop formed by securing member 28; see FIG. 9.

Clip 140 may have any of the features described above for clip 24. For example, the clip may have a U-shaped structure formed by proximal leaf portion 32, distal leaf portion 34, and bridge region 36. The proximal leaf portion may define a pair of apertures 142, 144 through which holes 46, 48 may be drilled in rib bone 26. The apertures, which may or may not be elongated to provide slots, may be longer and/or larger in diameter, than holes 46, 48, to permit axial compression of the rib bone when the securing member is tightened. In other words, the position of holes 46, 48 with respect to apertures 142, 144 may change as a region of rib bone 26 between holes 46, 48 is compressed axially. The length or characteristic dimension of the clip, measured parallel to through-axis 110, may be greater at bridge region 36 than the distance between holes 46, 48 and/or apertures 142, 144. In other embodiments, proximal leaf portion 32 may lack apertures 142, 144 and may taper more aggressively as the proximal leaf portion projects from the bridge region, such that holes 46, 48 can be formed lateral to, instead of through, the proximal leaf portion. Stated differently, holes 46, 48 can be formed outside the footprint of the clip on bone (i.e., outside the footprint of the proximal and/or distal leaf portions).

Bridge region 36 of clip 140 may define one or more openings 146 that expose rostral/superior surface areas 148 of the rib bone. Access to areas 148 may facilitate re-attachment of intercostal muscle to the rib bone.

Example 2

Implant with Pair of Clip Members

Figure 10:
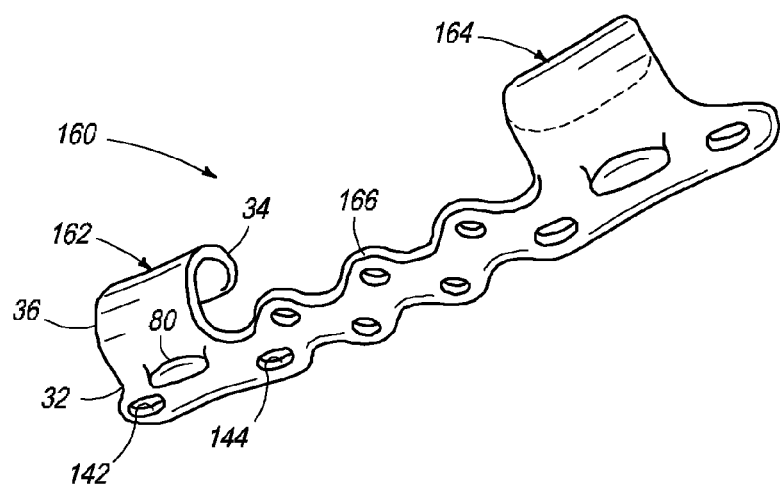
FIG. 10 is a perspective view of an exemplary embodiment of an implant for rib stabilization, with the implant including a pair of clip members connected integrally by a spanning member, in accordance with aspects of the present disclosure.

This example describes an exemplary implant 160 having a pair of clip members 162, 164 connected by a spanning member 166; see FIG. 10.

Each clip member 162, 164 may have any combination of the features described elsewhere herein for clips, such as leaf portions 32, 34, bridge region 36, a U-shape, hitching bracket 80, and apertures 142, 144. However, spanning member 166 may be positioned to span a discontinuity in the rib bone. (Each of clip members 162, 164 may or may not also span a discontinuity in the rib bone.) The spanning member may be attached to the rib bone with a securing member. In some cases, each clip member and the spanning member may be attached with a respective, distinct securing member.

Example 3

Selected Embodiments

This example describes selected embodiments of the present disclosure, presented as a series of numbered paragraphs.

1. A system for rib stabilization, comprising: (A) a clip member having a bridge region and a proximal leaf portion and a distal leaf portion connected to each other by the bridge region, the clip member being configured to be placed on a rib bone with the leaf portions disposed on opposite sides of the rib bone; and (B) a securing member to attach the clip member to the rib bone, the securing member including a suture.

2. The system of paragraph 1, wherein the distal leaf portion includes a retainer to hold the securing member.

3. The system of paragraph 2, wherein the retainer defines an axis that is parallel to a plane defined by a plate region of the distal leaf portion.

4. The system of paragraph 2 or 3, wherein the retainer defines a channel that extends along the axis.

5. The system of any of paragraphs 2 to 4, wherein a plate region of the distal leaf portion has an outer surface region, and wherein the retainer projects from the outer surface region.

6. The system of any of paragraphs 2 to 5, wherein the clip member defines a through-axis along which a rib bone extends after the clip member is placed on the rib bone, and wherein the retainer defines an aperture that is parallel to the through-axis.

7. The system of any of paragraphs 2 to 6, wherein the securing member extends through an aperture defined by the retainer.

8. The system of any of paragraphs 2 to 7, wherein the securing member is axially slideable in the retainer.

9. The system of any of paragraphs 1 to 8, wherein ends of the securing member are tied to one another.

10. The system of any of paragraphs 1 to 9, wherein the securing member is disposed in a loop.

11. The system of paragraph 10, wherein the loop is a suture loop.

12. The system of any of paragraphs 1 to 11, wherein the proximal leaf portion includes a bracket configured to engage the securing member.

13. The system of paragraph 12, wherein the securing member has a pair of ends, and wherein the bracket is configured to hold the securing member after the ends of the securing member have been fastened to each other and the securing member has been hooked onto the bracket.

14. The system of paragraph 12 or 13, wherein the securing member is disposed in a loop that is hooked onto the bracket.

15. The system of paragraph 14, wherein unhooking the loop from the bracket loosens the securing member.

16 The system of any of paragraphs 12 to 15, wherein the bracket projects upward when the bridge region is disposed above the leaf portions.

17. The system of any of paragraphs 1 to 16, wherein the securing member extends between the leaf portions at least twice without overlapping the bridge region.

18. The system of any of paragraphs 1 to 17, wherein the securing member is centered around an axis that extends through the bridge region.

19. The system of paragraph 18, wherein the axis is orthogonal to the bridge region.

20. The system of any of paragraphs 1 to 17, wherein the securing member extends between the leaf portions exactly twice and forms a loop.

21. The system of any of paragraphs 1 to 20, wherein the securing member is engaged with each leaf portion.

22. The system of paragraph 21, wherein the securing member is not in contact with the bridge region.

23. The system of any of paragraph 1 to 22, wherein the clip member includes at least one integral drill guide connected to a leaf portion.

24. The system of paragraph 23, wherein each drill guide is attached to the proximal leaf portion by a frangible connection.

25. The system of paragraph 24, wherein the proximal leaf portion thins at the frangible connection.

26. The system of any of paragraphs 23 to 25, wherein the clip member includes a pair of detachable drill guides.

27. The system of any of paragraphs 23 to 26, wherein each drill guide defines an aperture that is elongated transverse to a plane defined by a plate region of the proximal leaf portion.

28. The system of any of paragraphs 23 to 27, wherein each drill guide defines an aperture that is open at opposing ends and open along a side of the drill guide to form a slot.

29. The system of any of paragraphs 1 to 28, wherein the clip member is formed of a bioresorbable polymer.

30. The system of any of paragraphs 1 to 29, wherein the securing member is formed of a bioresorbable polymer.

31. The system of any of paragraphs 1 to 30, wherein the securing member includes a pair of ends tied together to form a knot.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of rib stabilization, comprising:
    selecting a clip member having a bridge region and a pair of leaf portions connected to each other by the bridge region;
    disposing the clip member on a rib bone such that the leaf portions at least partially cover a discontinuity of the rib bone and are disposed on opposite sides of the rib bone from one another;
    creating a pair of holes through the rib bone, wherein the discontinuity is located intermediate the pair of holes; and
    fastening ends of a securing member to one another to form a loop that extends through each of the holes and connects the clip member to the rib bone.

2. The method of claim 1, wherein the securing member includes a suture.

3. The method of claim 2, wherein the step of fastening ends includes a step of tying a pair of suture ends to one another.

4. The method of claim 1, wherein the leaf portions include a proximal leaf portion and a distal leaf portion, and wherein the distal leaf portion includes a retainer for the securing member.

5. The method of claim 4, wherein the distal leaf portion includes a plate region that defines a plane, and wherein the loop extends through the retainer parallel to the plane.

6. The method of claim 4, wherein the securing member extends through the retainer parallel to a longitudinal axis of the rib bone.

7. The method of claim 1, wherein the clip member includes a pair of integral drill guides connected to a proximal leaf portion, further comprising a step of forming holes through the rib bone coaxial with the drill guides, and a step of detaching the drill guides from the proximal leaf portion.

8. The method of claim 1, wherein the clip member includes a body formed collectively by the leaf portions and the bridge region, and wherein the bracket projects from the body.

9. The method of claim 1, wherein the leaf portions include a proximal leaf portion having an outer surface region that faces away from the rib bone, and wherein the step of hooking includes a step of hooking the loop onto a bracket projecting from the outer surface region of the proximal leaf portion.

10. The method of claim 1, further comprising a step of hooking the loop onto a bracket of the clip member to tension the loop.

11. The method of claim 10, wherein the step of hooking the loop applies axial compression to the rib bone between the pair of holes.

12. The method of claim 10, wherein the step of hooking the loop includes a step of producing a tensioned configuration of the securing member that urges the bridge region toward the rib bone, urges the leaf portions toward each other, and applies axial compression to the rib bone.

13. The method of claim 10, wherein the step of hooking produces a configuration in which an outer portion of the loop extends from an outer end of one of the holes to the bracket and from the bracket to an outer end of the other hole, without extending to an inner side of the rib bone.

14. The method of claim 13, wherein the step of hooking the loop repositions a central region of the outer portion of the loop closer to the bridge region.

15. The method of claim 14, wherein the leaf portions include a proximal leaf portion and a distal leaf portion, and wherein the proximal leaf portion includes the bracket and the distal leaf portion includes a retainer for the securing member, and wherein the pair of holes in the rib bone are located inferior to the bracket and the retainer after the step of hooking.

16. The method of claim 1, wherein the leaf portions are disposed on an inner side and an outer side of the rib bone, and wherein the loop extends from the inner side to the outer side of the rib bone only via the pair of holes.

17. A method of rib stabilization, comprising:
    selecting a clip member having a bridge region and proximal and distal leaf portions connected to each other by the bridge region, the distal leaf portion including a retainer;
    disposing the clip member on a rib bone with the proximal and distal leaf portions disposed on respective outer and inner sides of the rib bone and each at least partially covering a discontinuity of the rib bone such that the proximal and distal leaf portions face one another at the discontinuity, the rib bone extending through the clip member along a through-axis; and
    attaching the clip member to the rib bone with a securing member that extends at least twice between the leaf portions and that extends through the retainer of the distal leaf portion substantially parallel to the through-axis.

18. The method of claim 17, wherein the step of attaching the clip member includes a step of fastening ends of the securing member to each other and a step of hooking the securing member onto a bracket of the clip member after the step of fastening ends.

19. The method of claim 18, wherein the step of hooking applies axial compression to the rib bone.

20. The method of claim 18, wherein the step of hooking urges the bridge region toward the rib bone and urges the leaf portions toward each other.

21. A method of rib stabilization, comprising:
   selecting a clip member having a bridge region and also having a pair of leaf portions that are connected to each other by the bridge region;
   disposing the clip member on a rib bone such that the leaf portions at least partially cover a discontinuity of the rib bone and are disposed on opposite sides of the rib bone; and
   fastening ends of a securing member to one another to form a loop that connects the clip member to the rib bone;
   wherein the loop does not cross itself at any position spaced from the fastened ends of the loop.

* * * * *